United States Patent
Heikkilä et al.

(12) 
(10) Patent No.: US 6,262,318 B1
(45) Date of Patent: Jul. 17, 2001

(54) METHOD OF PRODUCING POLYOLS FROM ARABINOXYLAN-CONTAINING MATERIAL

(75) Inventors: Heikki Heikkilä, Espoo; Raimo Alen, Helsinki; Siru Kauko, Jyväskylä; Mirja Lindroos; Juha Nurmi, both of Kirkkonummi; Päivi Sarmala; Matti Tylli, both of Kantvik, all of (FI)

(73) Assignee: Xyrofin Oy, Espoo (FI)

( * ) Notice: Subject to any disclaimer, the term of this patent is extended or adjusted under 35 U.S.C. 154(b) by 0 days.

(21) Appl. No.: 09/431,426

(22) Filed: Nov. 1, 1999

(30) Foreign Application Priority Data

Nov. 18, 1998 (FI) .................................................... 982497

(51) Int. Cl.$^7$ ........................ C07C 29/141; C07C 29/149
(52) U.S. Cl. ......................... 568/864; 562/531; 564/863
(58) Field of Search ................... 568/863, 864; 562/531

(56) References Cited

U.S. PATENT DOCUMENTS

| | | | |
|---|---|---|---|
| 3,586,537 | 6/1971 | Steiner et al. | 127/37 |
| 3,784,408 | 1/1974 | Jaffe et al. | 127/37 |
| 4,008,285 | 2/1977 | Melaja et al. | 260/635 C |
| 4,066,711 | 1/1978 | Melaja et al. | 536/1 |
| 4,075,406 | 2/1978 | Melaja et al. | 260/635 C |
| 4,752,579 | 6/1988 | Arena et al. | 435/99 |
| 4,816,078 | 3/1989 | Schiweck et al. | 127/36 |
| 4,880,919 | 11/1989 | Kulprathipanja | 536/127 |
| 5,084,104 | 1/1992 | Keikkila et al. | 127/46.2 |
| 5,096,820 | 3/1992 | Leleu | 435/158 |
| 5,238,826 | 8/1993 | Leleu et al. | 435/105 |
| 5,563,303 | 10/1996 | Vuorinen | 568/864 |
| 5,631,150 | 5/1997 | Harkki et al. | 435/105 |

FOREIGN PATENT DOCUMENTS

| | | |
|---|---|---|
| 0 136 802 B1 | 4/1985 | (EP) . |
| 0 136 803 B1 | 4/1985 | (EP) . |
| 0 262 463 B1 | 4/1988 | (EP) . |
| 0 327 342 B1 | 8/1989 | (EP) . |
| 0 344 371 A1 | 12/1989 | (EP) . |
| 0 820 979 A1 | 1/1998 | (EP) . |
| 0 829 485 A1 | 3/1998 | (EP) . |
| WO 97/20860 | 6/1997 | (WO) . |
| WO 98/50589 | 11/1998 | (WO) . |
| WO99/57326 | 11/1999 | (WO) . |

OTHER PUBLICATIONS

"Synthesis of Some Esters and Lactones of Aldonic Acids", by W.J. Humphlett, Carbohyd. Res., 4 (1967), pp. 157–164.

"Preparation of meso–Erythritol and D–Erythronic Lactone from Periodate–Oxidized Starch", by Allene Jeanes, et al., contribution from the National Institute of Arthritis and Metabolic Diseases, et al., pp. 1565–1568 (1955).

"The Method of Oxidation and the Oxidation Products of 1–Arabinose and of 1–Xylose in Alkaline Solutions with Air and with Cupric Hydroxide", by J. U. Nef, et al., contribution from the Kent Chemical Laboratory of the University of Chicago, pp. 1638–1652 (1917).

German Publication No. 618164 (1935).

Jeanes et al., J. Org. Chem., 20, 1565–1568 (1955); and Humphlett, Carbohyd. Res., 4, 157–164 (1967).

*Primary Examiner*—Peter O'Sullivan
(74) *Attorney, Agent, or Firm*—Scully, Scott, Murphy & Presser

(57) ABSTRACT

The invention relates to a method of producing xylitol and erythritol from arabinoxylan-containing material. According to the invention, the arabinoxylan-containing material is hydrolyzed and xylose and arabinose are separated from the obtained hydrolysate, whereafter the xylose is reduced to xylitol, and the xylitol is recovered, and the arabinose is subjected to alkaline oxidation to obtain erythronic acid which is reduced to erythritol, and the erythritol is recovered.

15 Claims, No Drawings

METHOD OF PRODUCING POLYOLS FROM ARABINOXYLAN-CONTAINING MATERIAL

The invention relates to a method of producing polyols from xylan-containing hemicellulose, in particular the invention relates to a method of producing xylitol and erythritol from arabinoxylan-containing material.

Xylitol is a sugar alcohol which occurs in nature and which is most commonly produced by reducing xylose, and whose sweetness corresponds to "ordinary sugar", but whose calorie content (2.4 kcal/g) is lower than that of ordinary sugar. Small amounts of xylitol occur in many fruits and vegetables, and it is also produced by the human body as a normal metabolic product. The metabolic, odontological and technical properties of xylitol make it an extremely good special sweetener for a variety of uses, such as chewing gums, sweets, bakery products, etc. An example is the independence of xylitol metabolism of insulin metabolism, allowing also diabetics to use xylitol. Xylitol also has a slowing effect on bowel function and reduces nutrient absorption, making it usable in slimming diets. Furthermore, it has been found that xylitol is noncariogenic, even anticariogenic.

Despite the numerous advantages of xylitol, its use has been rather limited. This is due to the relatively high price of xylitol, which in turn results from high production costs.

Previously xylitol was mainly produced by hydrolyzing a material rich in xylan. A monosaccharide mixture, containing large amounts of xylose, is thus obtained. Thereafter, xylose is reduced to xylitol by catalytic reduction (hydrogenation), in general in the presence of a nickel catalyst, such as Raney nickel. The literature of the field describes numerous methods of producing xylose and/or xylitol from xylan-containing material. As examples can be given U.S. Pat. No. 3,784,408 (Jaffe et al.), U.S. Pat. No. 4,066,711 (Melaja et al.), U.S. Pat. No. 4,075,406 (Melaja et al.), U.S. Pat. No. 4,008,285 (Melaja et al.) and U.S. Pat. No. 3,586,537 (Steiner et al.). Xylitol can also be produced from glucose as disclosed in U.S. Pat. No. 5,631,150 (Harkki et al.) or from hexose as disclosed in U.S. Pat. Nos. 5,563,303, 5,238,826 and 5,096,820 and from oses and uloses as disclosed in WO 9,720,860.

In several plants the majority of hemicellulose is xylan, which can be hydrolyzed to xylose. A primary raw material of xylan is the hemicellulose of e.g. hardwood, corn cobs and bagasse, which mainly consists of xylan. Recently, there has been an increasing interest in the utilization of xylan and xylose obtained as by-products in pulp industry. Xylose is formed, for instance, in acid sulphite cookings, in which typical bases are $Mg^{2+}$, $Ca^{2+}$, $NH_4^+$ and $Na^+$. A cooking liquor of neutral sulphite cookings can also be used as a raw material after the xylo-oligomers of oligomeric and polymeric xylan have been hydrolyzed. In the cooking liquor of acid sulphite cookings the hemicelluloses are mainly in the form of monosaccharides.

When using sulphite cooking liquor as a raw material of xylose, the problem is the variability of cooking conditions. Depending on the conditions, hemicellulose of wood dissolves in different ways yielding smaller or greater amounts of xylose. Cooking conditions which yield little xylose, may yield considerable amounts of xylonic acid.

A drawback with the previous methods is that only the xylose-rich hemicellulose is utilized and the rest of the hemicellulose structures is left unutilized.

Like other sugar alcohols, erythritol is highly thermostable and acid stable. Like mannitol, it has poor solubility, and like xylitol, its solution heat is low.

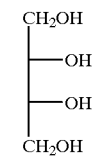

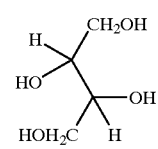

Erythrtol is a polyhydroxyalcohol occurring widely in nature, for instance, as a metabolic product and storage material in algae and fungi. Fruits, for instance melons, grapes and pear, contain erythritol. Various microorganisms, such as bacteria, fungi and yeasts, produce erythritol, and therefore it occurs in food products prepared by fermentation processes, such as wine and beer, and in processed vegetables, such as soya sauce.

Since erythritol is introduced into the system along with the food, it can be found in many tissues and fluids of the body, such as the lens tissue of the eye, blood serum, sperm, amniotic fluid and urine. In human urine it is the principal sugar alcohol.

Many osmophilic yeasts are able to produce polyhydroxyalcohols. Yeasts like this and yeast-like fungi are found as contaminants in substances with high sugar content, such as honey. Resistance against high sugar and salt content is typical of them.

Erythritol is prepared biotechnically by hydrolyzing wheat and corn starches to glucose which is fermented mainly to erythritol by means of an osmophilic yeast (*Moniliella pollinis*), as disclosed in EP 136,803, EP 136, 802, EP 262,463, and EP 327,342. The yield of the fermentation process is about 50% and e.g. ribitol or glycerol is formed as a by-product. The osmophilic property of yeast has a consequence that the dry solids content of the reaction liquor is high. From purified and concentrated liquor, it is possible to crystallize pure erythritol. A variety of other yeasts having osmophilic properties produce erythritol together with glycerol and/or D-arabinitol, but the problem is separation and purification of erythritol from the reaction mixture. Moreover, it has been found that certain yeasts yield acetoin as a by-product, the removal of which is difficult. A. Jeanes (*J. org. Chem* 20, 1565–1568, 1955) describes 15 preparation of erythritol from erythronic acid. The publication by W. J. Humphlett, *Carbohydrate Res.* 4, 157–164, 1967, describes preparation of erythronic acid from L-arabinose.

Erythritol, like other sugar alcohols used as sweeteners, such as sorbitol, maltitol and lactitol, is tooth-friendly and suitable for diabetics. Because of the small molecular size, erythritol reacts in metabolism in a totally different manner from other sugar alcohols. Consequently, the most important differences are its considerably lower energy content in comparison with other sugar alcohols and the system's higher tolerance to said substance.

The nutritional value of erythritol is considerably lower than that of other special sweeteners. Only 20% of erythritol can continue from the small intestine to the large intestine and therein only half of the substance, at most, converts to volatile fatty acids and further to energy to be used by the body.

On the average, 50 to 60% of the original energy content of other special sweeteners remains for use in the body, but of erythritol the percentage is only about 10, which corresponds to 0.3 kcal/g of the energy content.

Oral bacteria cannot utilize erythritol, as they cannot utilize other polyhydroxyalcohols either. In the tests conducted, it was found that oral bacteria, in particular the main cause of caries, *Streptococcus mutans*, cannot use erythritol for growth. Hence, it is possible to avoid the formation of organic acids and plaque, which contribute to the emergence of caries. This is why the use of erythritol as a sweetener makes the food products tooth-friendly.

In a 10% solution, the sweetness of erythritol is 60 to 70% as compared with cane sugar. The taste profile of erythritol is very similar to that of cane sugar, and it has no bitter after-taste. Therefore it suits well for improving the taste of other sweetening agents, such as aspartame.

It has now been found that xylitol and erythritol can be produced in an advantageous manner from an arabinoxylan-containing material.

β-D-xylo-pyranose units linked with a 1–4 glycosidic bond form the main chain of D-xylans. These polysaccharides occur in all plants and almost all plant parts. Proper D-xylan, formed from D-xylose alone, occurs rarely, and most D-xylan structures have other sugars as side chains.

One of the common side chains is L-arabinose, which in most cases is in the form of furanose. L-arabinose often forms the side chain alone, even though the chain may even comprise a plurality of sugar groups. In different plants, the proportion of L-arabinose and D-xylose varies greatly, depending on how branched said molecule is.

The present invention relates to a method of producing xylitol and erythritol from arabinoxylan-containing material. The method is characterized in that the arabinoxylan-containing material is hydrolyzed and xylose and arabinose are separated from the obtained hydrolysate, whereafter the xylose is reduced to xylitol and the xylitol is recovered, and the arabinose is subjected to alkaline oxidation to obtain erythronic acid which is reduced into erythritol and the erythritol is recovered.

Advantageously, said separation can be performed chromatographically. Xylitol and erythritol can be advantageously recovered by prior art crystallization methods.

Xylose and arabinose can be recovered as an intermediate product through crystallization. The crystallization can be suitably performed such that the xylose and arabinose fractions obtained from separation are first concentrated, whereafter the xylose and the arabinose are crystallized by using a suitable cooling program and seed crystals. A preferred alternative is to remove hexose from the obtained hydrolysate by yeast fermentation. One advantageous method to perform hydrolysis of hemicellulose is to employ xylanolytic enzymes. One advantageous method of alkaline oxidation is accomplished such that, during the reaction, erythronic acid crystallizes from the methanol-containing reaction mixture. In alkaline oxidation, anthraquinone can be used advantageously.

The method has an advantage that a by-product obtained from xylitol production can be used for producing erythritol. Arabinoxylan-containing material is advantageously corn or barley fibers. Hydrolysis is performed with an acid, advantageously using an aqueous solution of sulphuric acid at a temperature of about or exceeding 100° C. Separation of xylose and arabinose from the obtained hydrolysate is advantageously performed chromatographically, whereby a simulated moving bed (SMB) can be used. Chromatographic separation can be suitably performed in two separation steps, whereby in the first step the salts and part of the arabinose are removed, and in the second step the xylose and the arabinose are separated from one another. In the first separation, a column is advantageously filled with a strongly acid cation exchange resin, which is regenerated into the form of $Na^+$. The second separation is advantageously performed with a cation exchange resin, which is regenerated into the form of $Ca^{2+}$.

Reduction of xylose to xylitol is advantageously performed by catalytic reduction. Suitable catalysts include Raney-type catalysts and noble-metal catalysts, such as Ru, Pd and Pt. A suitable reduction temperature is 80 to 130° C., preferably 100 to 110° C. and the reduction is suitably carried out at a pressure of 30 to 60 bar, preferably 40 to 50 bar. Alkaline oxidation of arabinose to erythronic acid is preferably carried out in a methanol-water solution. A preferable oxidation temperature is 20 to 50° C. Reduction of erythronic acid is preferably carried out catalytically. Suitable catalysts include Ru, Rh, Pd and Pt, preferably Ru. A suitable reduction temperature is 80 to 130° C., preferably 100 to 110° C., and the reduction is carried out suitably at a pressure of 80 to 130 bar, preferably 100 to 110 bar.

Following examples illustrate the invention.

EXAMPLE 1

The raw material of hydrolysis was corn fiber having the following composition:

| | |
|---|---|
| dry substance (DS) | 95.3 g/100 g |
| ash | 0.6 % on DS |
| starch | 4.3 % on DS |
| metal cations (analysis by MS) | |
| Ca | 610 ppm on DS |
| K | 150 ppm on DS |
| Mg | 880 ppm on DS |
| Na | 67 ppm on DS |
| carbohydrates after hydrolysis (analysis by GLC) | |
| xylose | 39.2 % on DS |
| glucose | 15.6 % on DS |
| arabinose | 29.8 % on DS |
| mannose | 0.4 % on DS |
| galactose | 3.5 % on DS |

An amount of 2.0 kg DS of corn fiber was weighed into an acid resistant autoclave vessel. 10.0 l of 1% sulphuric acid was mixed with the fiber material, hydrolysis was started at 120° C. for 60 minutes. Warming up to a temperature of 120° C. took 55 minutes. The hydrolysate vessel rotated about its transverse axis thereby mixing the mixture. At the end of the hydrolysis, the autoclave was degassed. The solution phase was drained from the autoclave through a filter and was cooled. The solid residue was removed from the autoclave and washed with ion exchange water. The mixture was filtered and the filtrate was combined with the hydrolysate. The solution (=hydrolysate) was analysed for carbohydrates (by GLC). Yields from the hydrolysis and the composition of the hydrolysate are as follows:

TABLE 1

| | Yield (%/corn fiber DS) | Composition (%/hydrolysate DS) |
|---|---|---|
| Carbohydrates | | |
| glucose | 5.2 | 5.7 |
| xylose | 34.3 | 37.7 |
| galactose | 4.8 | 5.3 |
| rhamnose | — | — |

TABLE 1-continued

|  | Yield (%/corn fiber DS) | Composition (%/hydrolysate DS) |
|---|---|---|
| arabinose | 29.5 | 32.4 |
| mannose | 0.2 | 0.2 |
| Sulfate |  | 5.4 |

EXAMPLE 2

The raw material of hydrolysis was barley fiber after removal of starch. The raw material composition was as follows:

dry substance (DS) 95.5 g 1100 g
carbohydrates after hydrolysis (analysis by HPLC, $Pb^{+2}$ form ion exchange resin):

| glucose | 21.2 | % on DS |
| xylose | 21.2 | % on DS |
| galactose + rhamnose | 1.6 | % on DS |
| arabinose + mannose | 11.2 | % on DS |

An amount of 10 g DS of barley fiber was weighed into an acid resistant autoclave vessel. 150 ml of 0.25 w-% $H_2SO_4$ was mixed with the fiber (liquid to solid ratio 15:1). The hydrolysis was started at 142° C. for 1 hour. Warming up to a temperature of 142° C. took 25 minutes.

After hydrolysis, the vessel was cooled to room temperature. The content of the vessel was filtered. The hydrolysis residue on the filter was washed, and all washing waters were combined with the original filtrate. The filtrate was analysed for carbohydrates (by HPLC).

The carbohydrate yields from the hydrolysis and the composition of the hydrolysate are shown in Table 2.

TABLE 2

|  | Yield (%/barley fiber DS) | Composition (%/hydrolysate DS) |
|---|---|---|
| Carbohydrates |  |  |
| glucose | 2.1 | 1.6 |
| xylose | 18.7 | 31.0 |
| galactose + rhamnose | 1.3 | 2.1 |
| arabinose | 9.1 | 15.1 |
| Sulfate |  | 5.8 |
| Acetic acid |  | 1.6 |
| Nitrogen |  | 3.3 |

EXAMPLE 3

The solution prepared according to Example I was subjected to chromatographic separation in a chromatographic separation column. Two separation steps were used: the first separation ($Na^+$ form resin) for removing 5 the salts and part of the arabinose, and the second separation ($Ca^{2+}$ form resin) for separating the xylose and the arabinose from one another.

The separation was carried out in the chromatographic separation column as a batch process. The whole equipment consists of a feed tank, a feed pump, a heat exchanger, a column, an outlet pump, product containers, feed pipes and product pipes for feed solution and eluent water, and a control device and control valves for liquid to be discharged.

The first separation was carried out using a column filled with a strongly acid cation exchange resin (manufactured by Finex Oy, Finland) having a cross-linkage degree of 6.5% DVB and an average particle size of 0.41 mm. 1.5 $m^3$ of said resin was fed into the separation column with a diameter of 0.6 m and was regenerated to sodium ($Na^+$) form.

The process temperature was 65° C. and the flow rate was adjusted to 0.5 m/h.

The solution was concentrated to 30 g/100 g and pH of the feed solution was adjusted to 5.5 with 50 w-% NaOH solution and the solution was filtered with a pressure filter using diatomaceous earth as a filter aid.

The feed solution was pumped through the heat exchanger and the feeding device onto a resin bed. The feed solution was eluted by feeding ion exchange water to the top of the column. The density and conductivity of the outcoming solution was measured on-line, and on the basis of the obtained information the outflow was collected and divided into four fractions: residual fraction (containing salts and small amounts of sugars), recycle fraction (containing e.g. glucose, galactose and xylose), xylose fraction (containing most of the xylose and about half of the arabinose) and arabinose fraction.

The amount of dry substance as well as the xylose and arabinose content of the feed solution are shown in Table 3.

TABLE 3

COMPOSITIONS AND YIELDS

|  | Feed solution | Xylose fraction | Arabinose fraction |
|---|---|---|---|
| fraction DS, kg | 36 | 19.7 | 6.9 |
| DS content, g/100 g | 30 | 13.9 | 6.8 |
| xylose, % on DS | 36.2 | 52.5 | 9.6 |
| arabinose, % on DS | 31.2 | 28.9 | 79.7 |
| xylose, yield % |  | 79.3 | 5.1 |
| arabinose, yield % |  | 50.7 | 49.0 |

The xylose fraction obtained from the first separation was evaporated to a concentration of 30 g/100 g, and the second separation was carried out with a cation exchange resin regenerated to $Ca^{2+}$ ion form in order to purify xylose and arabinose. The cross-linkage degree of the resin (manufactured by Finex Oy, Finland) was 5.5% DVB and the average particle size was 0.31 mm.

The second separation was carried out in separation columns having a resin volume of 200 l. The equipment corresponded to that used in the first separation. The process temperature was 65° C. and the flow rate was adjusted to 0.6 m/h. The outflow was collected and divided into four fractions: residual fraction (containing small amounts of e.g. glucose, galactose, xylose) and recycle fraction (containing small amounts of e.g. glucose, galactose and xylose) and xylose fraction and arabinose fraction.

The amount of dry substance as well as xylose and arabinose content of the feed solution are given in Table 4.

TABLE 4

COMPOSITIONS AND YIELDS

|  | Feed solution | Xylose fraction | Arabinose fraction |
|---|---|---|---|
| fraction DS, kg | 6 | 3.5 | 1.5 |
| DS content, g/100 g | 30 | 12.0 | 8.7 |
| xylose, % on DS | 52.5 | 78.8 | 4.8 |
| arabinose, % on DS | 28.9 | 2.8 | 82.5 |

TABLE 4-continued

COMPOSITIONS AND YIELDS

| | Feed solution | Xylose fraction | Arabinose fraction |
|---|---|---|---|
| xylose, yield % | | 87.5 | 2.3 |
| arabinose, yield % | | 5.6 | 72.0 |

EXAMPLE 4

The xylose fraction obtained from the chromatographic separation was evaporated in a rotavapor (Büchi Rotavapor R-151) to 81.7% dry substance content. The mass (4 kg) was transferred into a 5-liter vertical, glass reaction vessel (70° C.). The vessel was provided with a jacket connected to a programmable water bath, and mixing was performed with an anchor-shaped mixer blade. An amount of 1 g of properly milled xylose was dosed as seed crystals into the mass. A linear 40-hour cooling program (from 70° C. to 25° C.) was started.

After cooling, the mass was mixed at 25° C. for about 5 hours, before the crystals were separated by centrifuging (Hettich Roto Silenta II centrifuge, basket diameter 24 cm, screen openings 0.15 mm) 3,500 rpm for 5 minutes. The crystal cake was washed with 80 ml distilled water.

The centrifuging results are shown in Table 5.

TABLE 5

| Mass introduced into centrifuge (g) | 743 |
|---|---|
| DS of the mass (w – %) | 81.8 |
| Purity of the mass (% on DS) | 78.3 |
| Crystal cake (g) | 295 |
| DS of the cake (w – %) | 98.9 |
| Purity of the cake (% on DS) | 99.2 |
| Purity of the run-off (% on DS) | 59.1 |
| Yield in centrifugation, DS/DS (w – %) | 48 |

EXAMPLE 5

The arabinose fractions from the chromatographic separations were evaporated to 71.2% dry substance content with a rotavapor (Büchi Rotavapor R-151). The mass (1.6 kg) was transferred into a 2-liter vertical, glass reaction vessel (65° C.). The vessel was provided with a thermal jacket connected to a programmable water bath, and mixing was performed with an anchor-shaped mixer blade. The mass was seeded with 100 g of milled arabinose, and a linear cooling program to 30° C. in 40 hours was started. At the end of the program, the mass was mixed at 30° C. for 6 hours, before the crystals were separated by centrifugation (Hettich Roto Silenta II centrifuge; basket diameter 24 cm). Rotation speed was 4,000 rpm for 5 minutes. The crystals were washed with 80 ml distilled water during centrifugation. The centrifuging results are shown in the following table.

TABLE 6

| Mass introduced into centrifuge (g) | 662 |
|---|---|
| DS of the mass (w – %) | 71.3 |
| Purity of the mass (% on DS) | 82.6 |
| Crystal cake (g) | 205 |
| DS of the cake (w – %) | 99.0 |

TABLE 6-continued

| Purity of the cake (% on DS) | 98.6 |
|---|---|
| Punty of the run-off (% on DS) | 70.3 |
| Yield in centrifugation, DS/DS (w – %) | 43 |

EXAMPLE 6

The L-arabinose obtained from the crystallization of L-arabinose was subjected to oxidation with oxygen.

| Test conditions: | |
|---|---|
| L-arabinose | 9.73 g |
| NaOH | 6.66 g |
| methanol-water solution (ratio by weight 1:1) total sample volume | 200 ml |
| reaction time | 10 h |
| mixing at 60 Hz speed for 1 sec, at 5-sec intervals | abt. 4.7 bar |
| oxygen pressure | |

The starting solution was prepared by dissolving sodium hydroxide (6.66 g) first in a small amount of methanol-water solution (ratio by weight 1:1) and by adding the cooled starting solution to an L-arabinose-methanol-water solution. The obtained solution (clear, slightly pale yellow) was introduced into a laboratory-scale reactor (400 ml) provided with a rotating (60 Hz) mixer. The sample solution in the closed reactor was flushed for one minute with oxygen flow, whereafter the reactor was pressurized with oxygen (abt. 4.7 bar). The oxygen line between the gas container and the reactor was kept open during the whole reaction. The reactor was adjusted to mix the sample continuously in 1-second sequences at 5-second intervals. The reaction time was 10 hours. The starting temperature of the reaction was adjusted to 22° C., i.e. the reaction was started at room temperature. At the end of the reaction, the temperature was 48° C.

The reaction product obtained was light, milk-like mixture, from which an amount was taken for analysis immediately after mixing. Thereafter said amount was centrifuged (1,500 rpm), whereby a white, fine precipitate and a clear solution were separated. The separated precipitate was dissolved in ion exchange water, which was combined for gas chromatographic analyses with the clear liquid phase previously separated in centrifugation.

From the above-prepared reaction product solution, inert arabinose and erythronic acid were analysed by gas chromatography (GC/FID) as silylated derivatives, using xylitol as an internal standard. The volatile acids (formic acid and acetic acid) were analysed as benzoic esters.

The results are shown in the following Table 7.

TABLE 7

Composition of a product obtained from L-arabinose in alkaline methanol-water solution in the presence of oxygen

| Compound | Proportion % on organic DS* |
|---|---|
| Arabinose** | 2.1 |
| Formic acid | 27.7 |
| Acetic acid | <0.1 |
| Erythronic acid | 59.9 |

TABLE 7-continued

Composition of a product obtained from L-arabinose in alkaline methanol-water solution in the presence of oxygen

| Compound | Proportion % on organic DS* |
|---|---|
| Others | 10.3 |
| Total | 100.0 |

*organic dry substance 65.1 g/l.
**conversion of arabinose was 97.2%

EXAMPLE 7

Xylose was dissolved and purified (decolorized and demineralized) using a strongly acid cation exchange resin (Dow 88$^R$) and a weakly basic anion exchange resin (Dow 66$^R$). Temperature during purification was 40° C. and the flow rate was 4 bed volumes/hour.

Hydrogenation was carried out using a batch-type autoclave (Medimex).

The hydrogenation conditions were as follows: temperature 110° C., xylose dry substance 50 g/100 g, hydrogen pressure 40 bar and catalyst load 10% catalyst slurry/xylose DS.

The catalyst used was Raney-type nickel catalyst (Chemcat J 10 GS$^R$).

The purity of the feed xylose was 99.5 on DS and purity of the xylitol product was 99.0% on DS.

EXAMPLE 8

The liquid material fed for hydrogenation process was prepared from L-arabinose using a basic oxidation process. The composition of the material fed for solution purification was the following: 59.9%/DS of erythronic acid, 27.7%/DS of formic acid, 2.1%/DS of arabinose.

The liquid was purified (decolorized, demineralized and decationized) using strongly acid cation exchange resin (Purolite C 155$^R$), polymeric adsorbent (Dowex Optipore$^R$) and weakly basic anion exchange resin (Purolite A 100$^R$). During a 10-liter cycle, 5 liters of each resin was used sequentially at a temperature of 40° C., the flow rate being 1 bed volume per hour. Thereafter, evaporation to remove the formic acid was carried out before hydrogenation.

The feed syrup concentration for hydrogenation was 19.5 g/100ml. Hydrogenation was carried out in following conditions: temperature was 100° C., hydrogen pressure was 100 bar, catalyst load 13% on DS (dry substance of catalyst and dry substance of supporufeed material). Hydrogenation was carried out using Medimex (5 liter) batch-type autoclave. The catalyst was Ru on carbon support (Engelhardt CP 56×L/R/WW).

The erythritol content of the syrup after hydrogenation was about 80 to 82% on dry substance.

EXAMPLE 9

Hydrogenated syrup, containing 80.3% erythritol on dry substance, was evaporated in a rotavapor (Büchi Rotavapor R-151). During evaporation, spontanous crystals were produced, whereby the evaporation process was interrupted. The mass temperature was 57° C. The KF dry substance content assayed on the mass sample was 70.9%. The mass was introduced into a vertical, 2-liter, glass reaction vessel whose temperature was set at 57° C. The vessel was provided with a thermal jacket connected to a programmable water bath, and mixing was carried out with an anchor-shaped mixer blade. The mass was cooled to 37° C. in 40 hours by a linear cooling program. At the end of the cooling program, the mass was mixed at 37° C. for 8 hours, before the crystals were separated by centrifugation (Hettich Roto Silenta II centrifuge; basket diameter 24 cm). The mass was centrifuged for 5 minutes at 4,000 rpm. During centrifugation, the crystals were washed with 80 ml distilled water. The centrifugation results are shown in Table 8.

TABLE 8

| Mass introduced into centrifuge (g) | 620 |
|---|---|
| DS of the mass (w – %) | 70.9 |
| Purity of the mass (% on DS) | 80.3 |
| Crystal cake (g) | 200 |
| DS of the cake (w – %) | 97.0 |
| Purity of the cake (% on DS) | 96.8 |
| Purity of the run-off (% on DS) | 65.4 |
| Yield in centrifugation, DS/DS (w – %) | 44 |

What is claimed is:

1. A method of producing xylitol and erythritol from arabinoxylan-containing material comprising hydrolyzing an arabinoxylan-containing material wherein a hydrolysate is obtained; separating xylose and arabinose from said hydrolysate; reducing said xylose to xylitol; recovering said xylitol; subjecting said arabinose to alkaline oxidation wherein erythronic acid is obtained; reducing said erythronic acid to erythritol; and recovering said erythritol.

2. A method as claimed in claim 1 wherein said alkaline oxidation is carried out with oxygen.

3. A method as claimed in claim 1 wherein said arabinoxylan-containing material is corn fibers.

4. A method as claimed in claim 1 wherein said arabinoxylan-containing material is barley fibers.

5. A method as claimed in claim 1 wherein said hydrolysis is carried out by contacting said arabinoxylan-containing material with sulfuric acid.

6. A method as claimed in claim 1 wherein said separation of xylems and arabinose is carried out chromatographically.

7. A method as claimed in claim 1 comprising purifying said xylose and/or arabinose by crystallization.

8. A method as claimed in claim 1 wherein said reduction of xylose is carried out catalytically with hydrogen.

9. A method as claimed in claim 1 wherein said xylitol is recovered by crystallization.

10. A method as claimed in claim 8 wherein said catalyst employed in said reduction of xvlose is Raney-Ni.

11. A method as claimed in claim 1 wherein said alkaline oxidation is carried out in a methanol-water solution.

12. A method as claimed in claim 11 wherein said alkaline oxidation is carried out with oxygen.

13. A method as claimed in claim 1 wherein said reduction of erytironic acid is carried out catalytically with hydrogen.

14. A method as claimed in claim 13 wherein said catalyst is Ru.

15. A method as claimed in claim 1 wherein said erythritol is recovered by crystallization.

* * * * *